United States Patent
Kabu et al.

(10) Patent No.: US 7,552,740 B2
(45) Date of Patent: Jun. 30, 2009

(54) METHOD OF MANAGING EASILY POLYMERIZABLE SUBSTANCE AND EASILY POLYMERIZABLE SUBSTANCE MANAGING APPARATUS

(75) Inventors: Yasuhiro Kabu, Saeki-gun (JP); Yoshimasa Ando, Ootake (JP); Nobuo Momodomi, Ootake (JP)

(73) Assignee: Mitsubishi Rayon Co., Ltd., Tokyo (JP)

( * ) Notice: Subject to any disclaimer, the term of this patent is extended or adjusted under 35 U.S.C. 154(b) by 120 days.

(21) Appl. No.: 10/506,216

(22) PCT Filed: Mar. 5, 2003

(86) PCT No.: PCT/JP03/02570

§ 371 (c)(1),
(2), (4) Date: May 3, 2005

(87) PCT Pub. No.: WO03/074461

PCT Pub. Date: Sep. 12, 2003

(65) Prior Publication Data

US 2005/0252557 A1  Nov. 17, 2005

(30) Foreign Application Priority Data

Mar. 6, 2002 (JP) ............................. 2002-061116

(51) Int. Cl.
*F17D 1/00* (2006.01)
(52) U.S. Cl. .................... 137/1; 137/15.05; 137/599.11
(58) Field of Classification Search ............. 137/15.05, 137/599.01, 599.09, 599.11, 599.14, 315.06, 137/599.05–505.07, 505.09, 505.11, 505.14, 137/1
See application file for complete search history.

(56) References Cited

U.S. PATENT DOCUMENTS

| 982,505 | A | * | 1/1911 | Koenig | ................... | 137/599.01 |
| 1,956,009 | A | * | 4/1934 | Diescher | ................. | 137/599.01 |
| 2,505,375 | A | * | 4/1950 | Wohlfarth | ............... | 137/599.14 |
| 3,010,316 | A | * | 11/1961 | Snyder | ................... | 137/599.05 |
| 3,038,449 | A | * | 6/1962 | Murphy, Jr. et al. | .... | 137/599.07 |

(Continued)

FOREIGN PATENT DOCUMENTS

EP  1 092 874  4/2001

(Continued)

*Primary Examiner*—Stephen M Hepperle
(74) *Attorney, Agent, or Firm*—Oblon, Spivak, McClelland, Maier & Neustadt, P.C.

(57) ABSTRACT

A method for handling an easily polymerizable substance and a device for handling an easily polymerizable substance are provided that prevent polymerization of the easily polymerizable substance in a bypass line by renewing the easily polymerizable substance retained in the bypass line of a flow control valve or flow meter installed in a line through which flows liquid containing an easily polymerizable substance. The method for handling an easily polymerizable substance renews liquid containing an easily polymerizable substance retained in the bypass line by intermittently opening and closing a bypass shutoff valve. The method for handling an easily polymerizable substance allows a portion of a liquid containing an easily polymerizable substance flowing through a line to flow through a bypass line by opening a bypass shutoff valve during handling of a liquid containing an easily polymerizable substance. The flow volume of the liquid containing an easily polymerizable substance that flows through the flow control valve or flow meter is 80% or more of the total flow volume of liquid containing an easily polymerizable substance that flows through the line.

13 Claims, 1 Drawing Sheet

U.S. PATENT DOCUMENTS

| | | | |
|---|---|---|---|
| 3,296,859 A * | 1/1967 | Stewart | 137/599.13 |
| 4,563,112 A * | 1/1986 | Mokuya et al. | 137/599.01 |
| 2001/0003783 A1 | 6/2001 | Nishimura et al. | |
| 2001/0015226 A1 | 8/2001 | Hamamoto et al. | |

FOREIGN PATENT DOCUMENTS

| | | |
|---|---|---|
| JP | 62-126245 | 8/1987 |
| JP | 2003-171343 | 6/2003 |

* cited by examiner

METHOD OF MANAGING EASILY POLYMERIZABLE SUBSTANCE AND EASILY POLYMERIZABLE SUBSTANCE MANAGING APPARATUS

TECHNICAL FIELD

The present invention relates to a method for handling easily polymerizable substances and a device for handling easily polymerizable substances that improve on the handling method of a flow control valve or flow meter provided in a line through which a liquid flows that contains an easily polymerizable substance such as (meth)acrylic acid, (meth)acrylate ester or (meth)acrolein, a bypass line of the flow control valve or flow meter, and a shutoff valve provided in the bypass line.

The present application is based on Japanese Patent Application No. 2002-61116, the contents of which are incorporated herein.

BACKGROUND ART

Similar to the case of substances other than easily polymerizable substances, distribution of liquids such as the transfer of liquid or feeding of liquid is carried out in the production processes of easily polymerizable substances such as (meth)acrylic acid, (meth)acrylate esters and (meth)acrolein.

"Easily polymerizable substances" polymerize extremely easily and polymers form easily during their production and distribution or other forms of handling. Therefore, polymerization inhibitors are added to easily polymerizable substances so that they can be handled while inhibiting their polymerization. If a polymerization inhibitor is added to an easily polymerizable substance, polymerization is inhibited even if it is allowed to remain for a fixed period of time in a pipe or other form of line used for its distribution. Pipes and so forth used for distribution of liquids containing easily polymerizable substances are designed and produced on the basis of this premise.

In order to ensure smooth distribution of liquid containing easily polymerizable substances, it is preferable that the easily polymerizable substance flows through a pipe or other type of line within a predicted retention time.

A flow control valve or flow meter is provided at an intermediate location in a line used for distribution of a liquid containing an easily polymerizable substance in order to ensure smooth operation of a production device and so forth. This flow control valve or flow meter may malfunction during the course of use. Consequently, the flow of liquid containing an easily polymerizable substance must be temporarily interrupted during repair or replacement of the flow control valve or flow meter. Therefore, a shutoff valve is typically provided in a line upstream or downstream from the flow meter or flow control valve in order to stop the flow of liquid containing an easily polymerizable substance.

When repairing or replacing the flow control valve or flow meter, the flow control valve or flow meter is repaired or replaced after closing a shutoff valve provided upstream or downstream there from to temporarily interrupt the flow of liquid containing an easily polymerizable substance.

In addition, in the case of having a considerable effect on the operation of a production device and so forth when the flow of the liquid containing an easily polymerizable substance is interrupted, a method is typically employed in which a bypass line is provided for the flow control valve or flow meter, and a shutoff valve is provided in this bypass line.

FIG. 1 is a schematic block drawing showing an example of a line through which flows a liquid containing an easily polymerizable substance. In addition, FIG. 2 is a schematic block drawing showing another example of a line through which flows a liquid containing an easily polymerizable substance.

In the lines shown in FIGS. 1 and 2, during the time flow control valve 2 or flow meter 3 provided in line 1 is operating normally, liquid containing an easily polymerizable substance flows by opening upstream shutoff valve 4 and downstream shutoff valve 5, and closing bypass shutoff valve 7 provided in bypass line 6.

The reason for allowing the liquid containing an easily polymerizable substance to flow by closing bypass shutoff valve 7 in this manner is because the entire amount of the liquid containing an easily polymerizable substance is allowed to flow through flow control valve 2 or flow meter 3, the flow rate is accurately controlled in flow control valve 2, and the flow rate is accurately indicated in flow meter 3.

In this type of line, in the case flow control valve 2 or flow meter 3 has malfunctioned, first bypass shutoff valve 7 is opened to ensure a flow of liquid containing an easily polymerizable substance to a degree that does not have a considerable effect on the operation of a production device and so forth. Next, upstream shutoff valve 4 and downstream shutoff valve 5 are closed to interrupt the flow of the easily polymerizable substance through line 1 and allow repair or replacement of flow control valve 2 or flow meter 3.

However, if bypass shutoff valve 7 is completely closed while liquid containing an easily polymerizable substance is flowing through line 1, the liquid containing an easily polymerizable substance remaining in bypass line 6 can no longer be renewed, and as a result, the liquid containing an easily polymerizable substance ends up remaining in bypass line 6 beyond the predicted retention time. If an easily polymerizable substance remains in bypass line 6 for a long period of time, it polymerizes and forms a polymer resulting in this polymer clogging bypass line 6. When bypass line 6 becomes clogged, bypass line 6 cannot be used when repairing or replacing flow control valve 2 or flow meter 3, thereby forcing operation of the production device and so forth to be temporarily interrupted and having a considerable effect on the factory overall.

DISCLOSURE OF THE INVENTION

In consideration of the aforementioned circumstances, an object of the present invention is to provide a method for handling easily polymerizable substances and a device for handling easily polymerizable substances that prevent polymerization of an easily polymerizable substance in a bypass line by renewing liquid containing an easily polymerizable substance retained in a bypass line of a flow control valve or flow meter installed in a line through which flows a liquid containing an easily polymerizable substance.

The aforementioned object can be achieved by a method for handling an easily polymerizable substance comprising a step of renewing liquid containing an easily polymerizable substance retained in a bypass line by intermittently opening and closing a shutoff valve when liquid containing an easily polymerizable substance flows through a line provided with a flow control valve or flow meter, the bypass line of the flow control valve or the flow meter, and the shutoff valve provided in the bypass line.

The aforementioned object can be achieved by a method for handling an easily polymerizable substance comprising a step of allowing a portion of a liquid containing an easily polymerizable substance flowing through a line to flow through a bypass line by opening a shutoff valve when liquid containing an easily polymerizable substance flows through the line provided with a flow control valve or flow meter, the bypass line of the flow control valve or flow meter, and the shutoff valve provided in the bypass line.

In the aforementioned method for handling an easily polymerizable substance, the flow volume of the liquid containing an easily polymerizable substance that flows through the flow control valve or flow meter is preferably 80% or more of the total flow volume of liquid containing an easily polymerizable substance that flows through the line.

The aforementioned easily polymerizable substance is preferably one or more types selected from the group consisting of (meth) acrylic acid, (meth)acrylate ester and (meth) acrolein.

The aforementioned object can be achieved by a device for handling an easily polymerizable substance provided with a line through which a liquid containing an easily polymerizable substance flows and which is provided with a flow control valve or flow meter, a bypass line of the flow control valve or flow meter, and a shutoff valve provided in the bypass line; wherein the device has a mechanism by which a liquid containing an easily polymerizable substance retained in the bypass line is renewed by intermittently opening and closing the shutoff valve.

The aforementioned object can be achieved by a device for handling an easily polymerizable substance provided with a line through which a liquid containing an easily polymerizable substance flows and which is provided with a flow control valve or flow meter, a bypass line of the flow control valve or flow meter, and a shutoff valve provided in the bypass line, wherein the device has a mechanism by which a portion of the liquid containing an easily polymerizable substance that flows through the line is allowed to flow through the bypass line by opening the shutoff valve during handling of liquid containing an easily polymerizable substance.

In the aforementioned device for handling an easily polymerizable substance, the flow volume of the liquid containing an easily polymerizable substance that flows through the flow control valve or flow meter is preferably 80% or more of the total flow volume of the liquid containing an easily polymerizable substance that flows through the line.

BEST MODE FOR CARRYING OUT THE INVENTION

Figure 1:
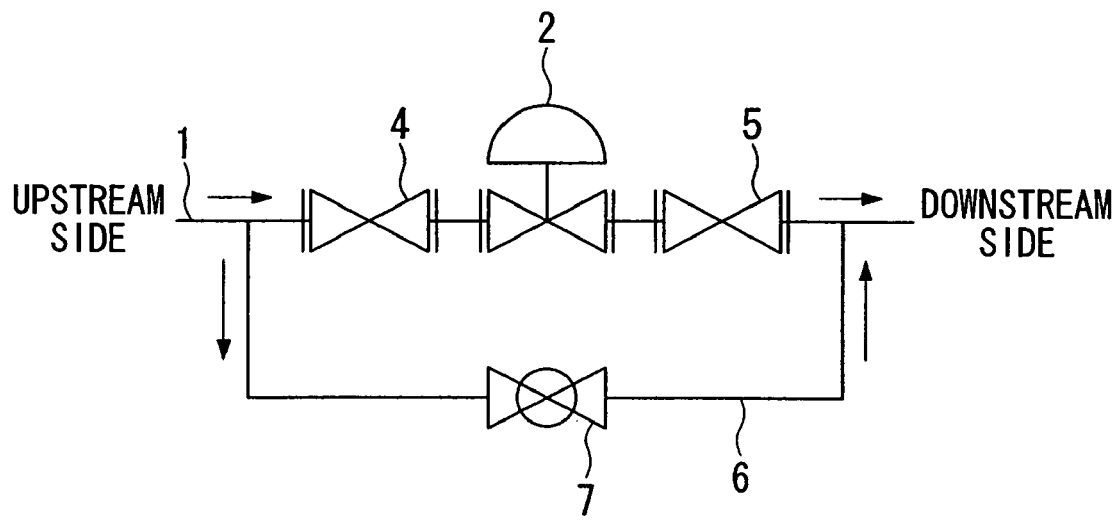
FIG. 1 is a schematic block drawing showing an example of a line through which flows a liquid containing an easily polymerizable substance.
Figure 2:
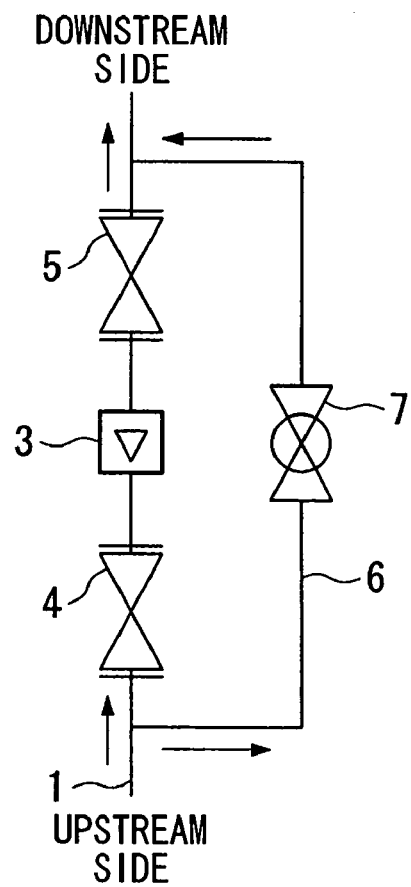
FIG. 2 is a schematic block drawing showing another example of a line through which flows a liquid containing an easily polymerizable substance.

The following provides a detailed explanation of the present invention using FIGS. 1 and 2.

As shown in FIGS. 1 and 2, the device for handling an easily polymerizable substance of the present invention is provided with a line through which flows a liquid containing an easily polymerizable substance that is provided with a flow control valve 2 or flow meter 3, a bypass line 6 thereof, a bypass shutoff valve 7 provided in bypass line 6, an upstream shutoff valve 4 and a downstream shutoff valve 5.

Examples of a device for handling an easily polymerizable substance of the present invention include a distillation device, extraction device, absorption device, evaporation device, decanter, compressor, pressure reducer and pump used to synthesize, purify, hold (store) or distribute an easily polymerizable substance.

In a first embodiment of a device for handling an easily polymerizable substance of the present invention, a liquid containing an easily polymerizable substance retained in bypass line 6 is renewed by intermittent opening and closing of a bypass shutoff valve 7 of the line provided in this device.

In the device for handling an easily polymerizable substance of this embodiment, flow through bypass line 6 is normally completely blocked by bypass shutoff valve 7, the entire amount of liquid containing an easily polymerizable substance flows through flow control valve 2 or flow meter 3, flow control valve 2 accurately controls the flow volume, and flow meter 3 accurately indicates the flow volume. Liquid containing an easily polymerizable substance retained in bypass line 6 is renewed by intermittently opening bypass shutoff valve 7 and allowing a portion of the liquid containing an easily polymerizable substance that flows through line 1 to pass through bypass line 6.

The frequency at which bypass shutoff valve 7 is intermittently opened and closed should be suitably set according to the type of easily polymerizable substance handled, the amount of polymerization inhibitor added thereto and so forth in consideration of the ease of polymerization of the easily polymerizable substance retained in bypass line 6. Bypass shutoff valve 7 preferably opens and closes regularly. The period of this regular opening and closing is preferably suitably set within the range from once an hour to once a year, and more preferably suitably set within the range of once every 8 hours to once a month.

In addition, although there are no particular limitations on the time required for opening and closing of bypass shutoff valve 7, it should be suitably set within a range that does not have an effect on processes upstream and downstream in the line. Normally, opening and closing of bypass shutoff valve 7 is preferably carried out within 10 seconds, and as a result, effects on upstream and downstream processes can be held to a minimum.

In addition, there are no particular limitations on the method for intermittently opening and closing bypass shutoff valve 7. A solenoid valve and so forth may be used for bypass shutoff valve 7 and its opening and closing may be controlled automatically by a control device, or bypass shutoff valve 7 may be opened and closed manually.

In this manner, according to the device for handling an easily polymerizable substance of this embodiment, by renewing liquid containing an easily polymerizable substance retained in bypass line 6 by intermittent opening and closing of a bypass shutoff valve 7, the formation of a polymer due to polymerization by the easily polymerizable substance retained in bypass line 6 and this polymer causing bypass line 6 to become clogged are prevented.

In a second embodiment of a device for handling an easily polymerizable substance of the present invention, a portion of a liquid containing an easily polymerizable substance that flows through a line is made to continuously flow through a bypass line 6 by opening a bypass shutoff valve 7 of the line provided in this device during handling of a liquid containing an easily polymerizable substance.

In the device for handling an easily polymerizable substance of this embodiment, bypass shutoff valve 7 is continuously opened a little during use of the device for handling an easily polymerizable substance, the flow volume of the liquid containing an easily polymerizable substance that flows through a flow control valve 2 or flow meter 3 is made to be 80% or more of the total flow volume of easily polymerizable substance that flows through line 1, and a portion of the liquid containing an easily polymerizable substance that flows through line 1 is made to flow through bypass line 6 to prevent the liquid containing an easily polymerizable substance from being retained in bypass line 6.

At this time, although the flow volume of the liquid containing an easily polymerizable substance that flows through flow control valve 2 or flow meter 3 is preferably 90% or more of the total flow volume of liquid containing an easily polymerizable substance that flows through line 1, it must not be 100%. If the flow volume of liquid containing an easily polymerizable substance that flows through flow control valve 2 or flow meter 3 is 100% of the total flow volume, then there is no flow of easily polymerizable substance through bypass line 6 and as a result, easily polymerizable substance is retained for a long period of time in bypass line 6, thereby making this undesirable. Thus, the flow volume of liquid containing an easily polymerizable substance that flows through flow control valve 2 or flow meter 3 is more preferably 90 to 99.5% of the total flow volume.

If the flow volume of liquid containing an easily polymerizable substance that flows through flow control valve 2 or flow meter 3 is 80% or more of the total flow volume of liquid containing an easily polymerizable substance that flows through line 1, then the flow volume of liquid containing an easily polymerizable substance that flows through flow control valve 2 or flow meter 3 can be secured to an industrially satisfactory degree, namely to a degree that the flow volume can be accurately controlled by flow control valve 2, or to a degree that the flow volume can be accurately measured by flow meter 3. Thus, if the aforementioned flow volume is less than 80%, then the flow volume of liquid containing an easily polymerizable substance is inadequate, and the control and measurement of flow volume cannot be carried out accurately.

In addition, another example of a method for accurately securing an industrially satisfactory flow volume of liquid containing an easily polymerizable substance that flows through flow control valve 2 or flow meter 3 consists of inserting an orifice that limits the flow volume through bypass line 6. However, this method is not preferable since the flow volume of liquid containing an easily polymerizable substance able to flow through bypass line 6 decreases thereby preventing bypass line 6 from fulfilling its inherent role during repair or replacement of flow control valve 2 or flow meter 3.

In this manner, according to the device for handling an easily polymerizable substance of this embodiment, by continuously opening bypass shutoff valve 7 a little during use of the device for handling an easily polymerizable substance to allow a portion of liquid containing an easily polymerizable substance that flows through line 1 to flow through bypass line 6, the formation of a polymer due to polymerization by the easily polymerizable substance retained in bypass line 6 and this polymer causing bypass line 6 to become clogged are prevented.

A liquid containing an easily polymerizable substance that is handled in the device for handling an easily polymerizable substance of the present invention refers to a liquid that contains 1% by weight or more of an easily polymerizable substance. In addition, examples of substances other than an easily polymerizable substance that compose the liquid containing an easily polymerizable substance include water and various organic solvents.

In addition, there are no particular limitations on the easily polymerizable substance handled in the device for handling an easily polymerizable substance of the present invention provided it is a substance that polymerizes easily, an example of such a substance is a polymerizing vinyl compound. The device for handling an easily polymerizable substance of the present invention is extremely effective in the case the easily polymerizable substance is (meth)acrylic acid, (meth)acrylate ester or (meth)acrolein in particular.

Examples of polymerizing vinyl compounds include unsaturated carboxylic acids such as (meth)acrylic acid; alkyl (meth)acrylates such as methyl(meth)acrylate, normal-butyl (meth)acrylate, isobutyl(meth)acrylate, tertiary-butyl(meth) acrylate, 2-ethylhexyl(meth)acrylate, lauryl(meth)acrylate, tridecyl(meth)acrylate and stearyl(meth)acrylate; alicyclic, aromatic ring, heterocyclic and vinyl group-containing (meth)acrylates such as cyclohexyl(meth)acrylate, benzyl (meth)acrylate, isobornyl(meth)acrylate, glycidyl(meth) acrylate, tetrahydrofurfuryl(meth)acrylate and aryl(meth) acrylate; hydroxyl or alkoxyl group-containing (meth) acrylates such as hydroxyethyl(meth)acrylate, hydroxypropyl(meth)acrylate, 2-methoxyethyl (meth) acrylate and 2-ethoxyethyl (meth) acrylate, multifunctional (meth)acrylates such as ethylene glycol di(meth)acrylate, triethylene glycol di(meth)acrylate, 1,3-butylene glycol di(meth)acrylate, 1,6-hexanediol di(meth)acrylate, polypropylene glycol di(meth)acrylate and trimethylol propane tri (meth)acrylate; carboxylic acid-containing (meth)acrylates such as 2-(meth)acryloyl oxyethyl phthalate and 2-(meth) acryloyl oxyethyl hexahydrophthalate; dialkylaminoethyl (meth)acrylates such as dimethylaminoethyl(meth)acrylate, dimethylaminoethyl(meth)acrylate methyl chloride, dimethylaminoethyl(meth)acrylate benzyl chloride and diethylaminoethyl(meth)acrylate; halogenated alkyl(meth)acrylates such as trifluoromethyl(meth)acrylate and heptadecafluorodecyl(meth)acrylate; and unsaturated aldehydes such as (meth)acrolein. The easily polymerizable substance may be present alone or as a mixture of a plurality of compounds.

A polymerization inhibitor such as a radical substance such as diphenylpicrylhydrazyl, phenol derivative, benzoquinone derivative or nitro compound is normally added at about 0.2.5 to 100 ppm to these easily polymerizable substances.

A polymerization inhibitor effective for a liquid containing an easily polymerizable substance is also added in the handling of an easily polymerizable substance using a device for handling an easily polymerizable substance to prevent expected polymerization of the easily polymerizable substance during the retention period in the device for handling an easily polymerizable substance. However, a large amount of polymerization inhibitor is required to prevent polymerization of the easily polymerizable substance that has been retained for a long period of time in the bypass line without being renewed. The use of a large amount of polymerization inhibitor is undesirable since it leads to increased costs.

Thus, if a liquid containing an easily polymerizable substance retained in a bypass line is renewed by allowing the liquid containing an easily polymerizable substance to flow through the bypass line by intermittently opening and closing a bypass shutoff valve in the manner of the device for handling an easily polymerizable substance of the present invention, or if a portion of a liquid containing an easily polymerizable substance flowing through a line is allowed to flow through a bypass line by continuously opening a bypass shutoff valve a little while the device is being used, polymerization of the easily polymerizable substance retained in the bypass line can be prevented without using a large amount of polymerization inhibitor. Thus, since the bypass line can be used effectively during repair or replacement of a flow control valve or flow meter, the entire factory does not have to be shut down at that time, thereby making it possible to reduce costs.

EXAMPLES

The following clarifies the effects of the present invention by indicating specific examples using FIGS. 1 and 2.

Example 1

A liquid in which polymerization inhibitors in the form of 5 mg/l of phenothiazine and 10 mg/l of hydroquinone were added to crude methacrylic acid having a purity of 99% by weight was allowed to flow through an area flow meter capable of measuring from 2 to 10 kl/h at 35° C. to measure its flow volume.

Flow volume was measured continuously for about 2 years while renewing the liquid retained in a bypass line 6 by opening a bypass shutoff valve 7 provided in bypass line 6 in the manner shown in FIG. 2 for about 2 seconds once every three days.

When bypass line 6 was inspected following completion of measuring flow volume, there was no polymer of methacrylic acid present therein, and clogging of bypass line 6 by the polymer was not confirmed during measurement of flow volume.

Example 2

The flow volume of a liquid containing methyl methacrylate having a purity of 99.99% by weight to which a polymerization inhibitor had not been added was controlled by a flow control valve capable of regulating flow volume to 5 to 15 kl/h at a temperature of 15° C. for operation of a factory line. The factory line was operated continuously for about 2 years while renewing the liquid retained in a bypass line 6 by opening a bypass shutoff valve 7 provided in bypass line 6 in the manner shown in FIG. 1 for about 2 seconds once every three days.

When bypass line 6 was inspected following completion of operation, there was no polymer of methyl methacrylate present therein, and clogging of bypass line 6 by the polymer was not confirmed during operation.

Example 3

A liquid in which polymerization inhibitors in the form of 50 mg/l of hydroquinone was added to methacrolein having a purity of 90% by weight was allowed to flow through an area flow meter capable of measuring from 4 to 14 kl/h at 5° C. to measure its flow volume.

Flow volume was measured continuously for about 2 years while renewing the liquid retained in a bypass line 6 by opening a bypass shutoff valve 7 provided in bypass line 6 in the manner shown in FIG. 2 for about 1 second once every three days.

When bypass line 6 was inspected following completion of measuring flow volume, there was no polymer of methacrolein present therein, and clogging of bypass line 6 by the polymer was not confirmed during measurement of flow volume.

Comparative Example 1

The flow volume of a liquid containing crude methacrylic acid was measured in the same manner as Example 1 with the exception of not opening and closing bypass shutoff valve 7 provided in bypass line 6 in the manner shown in FIG. 2.

When bypass shutoff valve 7 provided in bypass line 6 was opened since the area flow meter malfunctioned three months after starting measurement, bypass line 6 was clogged and liquid containing crude methacrylic acid was unable to flow through. Thus, the entire factory had to be shut down to replace the area flow meter. When the inside of bypass line 6 was inspected, the entire bypass line 6 was replaced since it was clogged with polymer of methacrylic acid.

Comparative Example 2

The flow volume of a liquid containing methyl methacrylate was controlled in the same manner as Example 2 with the exception of not opening and closing bypass shutoff valve 7 provided in bypass line 6 in the manner shown in FIG. 1.

When bypass shutoff valve 7 provided in bypass line 6 was opened since controllability of flow control valve 2 became poor six months after starting operation, bypass line 6 was clogged and liquid containing methyl methacrylate was unable to flow through. Thus, the entire factory had to be shut down to perform maintenance on flow control valve 2. When the inside of bypass line 6 was inspected, it was found to be clogged with polymer of methyl methacrylate. The adherence of this polymer directly on flow control valve 2 accompanying flow of liquid containing methyl methacrylate was the direct cause of poor controllability. Therefore, the entire bypass line 6 was replaced.

Comparative Example 3

The flow volume of a liquid containing methacrolein was measured in the same manner as Example 3 with the exception of not opening and closing bypass shutoff valve 7 provided in bypass line 6 in the manner shown in FIG. 2.

When bypass shutoff valve 7 provided in bypass line 6 was opened since the area flow meter malfunctioned three months after starting measurement, bypass line 6 was clogged and liquid containing methacrolein was unable to flow through. Consequently, the entire factory had to be shut down to replace the area flow meter. When the intermediate section of bypass line 6 was inspected, the entire bypass line 6 was replaced since it was clogged with polymer of methacrolein.

On the basis of the results of Examples 1 through 3 and Comparative Examples 1 through 3, if liquid retained in bypass line 6 is renewed by intermittently opening bypass shutoff valve 7, bypass line 6 was confirmed to not be clogged by polymer.

INDUSTRIAL APPLICABILITY

As has been explained above, since the method for handling an easily polymerizable substance of the present invention renews a liquid containing an easily polymerizable substance retained in a bypass line by intermittently opening and closing a shutoff valve in a line provided with a flow control valve of flow meter, bypass line of the flow control valve or flow meter and shutoff valve provided in the bypass line, retention of liquid containing an easily polymerizable substance beyond a predicted retention time in a bypass line is eliminated, thereby preventing the liquid containing an easily polymerizable substance from polymerizing resulting in the polymer clogging the bypass line.

In addition, since the method for handling an easily polymerizable substance of the present invention allows a portion of a liquid containing an easily polymerizable substance that flows through a line to flow through a bypass line by opening a shutoff valve during handling of a liquid containing an easily polymerizable substance in a line through which a liquid containing an easily polymerizable substance flows that is provided with a flow control valve or flow meter, a bypass line of the flow control valve or flow meter, and a shutoff valve provided in the bypass line, the easily polymerizable substance is not retained in the bypass line and polymerization of the easily polymerizable substance can be prevented. Thus, the bypass line does not become clogged with a polymer of the easily polymerizable substance.

In the aforementioned method for handling an easily polymerizable substance, if the flow volume of the liquid containing an easily polymerizable substance that flows through the flow control valve or flow meter is 80% or more of the total flow volume of liquid containing an easily polymerizable substance that flows through the line, polymerization of the easily polymerizable substance can be prevented while securing a flow volume of the liquid containing an easily polymerizable substance that flows the flow control valve or flow meter to a degree that control and measurement of flow volume can be carried out accurately.

In the device for handling an easily polymerizable substance of the present invention, since a liquid containing an easily polymerizable substance retained in a bypass line is renewed by intermittently opening and closing a shutoff valve in a device for handling an easily polymerizable substance provided with a line through which a liquid containing an easily polymerizable substance that is provided with a flow control valve or flow meter, a bypass line of the flow control valve or flow meter, and a shutoff valve provided in the bypass line, retention of liquid containing an easily polymerizable substance beyond a predicted retention time in a bypass line is eliminated, thereby preventing the liquid containing an easily polymerizable substance from polymerizing resulting in the polymer clogging the bypass line.

Since the device for handling an easily polymerizable substance of the present invention allows a portion of a liquid containing an easily polymerizable substance that flows through a line to flow through a bypass line by opening a shutoff valve during handling of a liquid containing an easily polymerizable substance in device for handling an easily polymerizable substance provided with a line through which a liquid containing an easily polymerizable substance flows that is provided with a flow control valve or flow meter, a bypass line of the flow control valve or flow meter, and a shutoff valve provided in the bypass line, the easily polymerizable substance is not retained in the bypass line and polymerization of the easily polymerizable substance can be prevented. Thus, the bypass line does not become clogged with a polymer of the easily polymerizable substance.

What is claimed is:

1. A method for handling an easily polymerizable substance, comprising:
    renewing a liquid comprising an easily polymerizable substance retained in a bypass line by opening and closing a shutoff valve provided in the bypass line intermittently while the liquid containing an easily polymerizable substance flows through a line provided with a flow control valve or flow meter, to provide some of the liquid comprising an easily polymerizable substance to the bypass line of the line provided with the flow control valve or the flow meter while the shutoff valve provided in the bypass line is open,
    wherein the time between intermittent opening and closing the shutoff valve provided in the bypass line is determined to provide a retention time of the easily polymerizable substance retained in by the bypass line to be less than a time where polymerization would lead to formation of polymer clogging the line, and
    the easily polymerizable substance is a polymerizable vinyl compound or a mixture of polymerizable vinyl compounds.

2. A method for handling an easily polymerizable substance comprising:
    diverting a first portion of a liquid comprising an easily polymerizable substance flowing through a line provided with a flow control valve or flow meter to flow through a bypass line by opening a shutoff valve provided in the bypass line while maintaining a flow of a second portion of the liquid comprising an easily polymerizable substance through the line provided with the flow control valve or flow meter,
    wherein the first portion of the liquid comprising an easily polymerizable substance diverted to flow through the bypass line is at least a percentage of total volume flow resulting in that the retention time of the liquid comprising an easily polymerizable substance in the bypass line is less than a time where polymerization would lead to formation of polymer clogging the line, and
    the easily polymerizable substance is a polymerizable vinyl compound or a mixture of polymerizable vinyl compounds.

3. The method for handling an easily polymerizable substance according to claim 2, wherein the flow of the second portion has a volume that is in the range from 80% to 99.5% of the total volume flow.

4. The method for handling an easily polymerizable substance according to any one of claims 1 through 3, wherein the polymerizable vinyl compound or a mixture of polymerizable vinyl compounds is at least one selected from the group consisting of (meth)acrylic acid, a (meth)acrylate ester and an unsaturated aldehyde.

5. The method for handling an easily polymerizable compound according to claim 4, wherein the (meth)acrylate ester is at least one selected from the group consisting of methyl (meth)acrylate, normal-butyl(meth)acrylate, isobutyl(meth)acrylate, tertiary-butyl(meth)acryl ate, 2-ethylhexyl(meth)acryl ate, lauryl(meth)acryl ate, tridecyl(meth)acrylate, stearyl(meth)acryl ate, cyclohexyl(meth)acrylate, benzyl (meth)acrylate, isobornyl(meth)acrylate, glycidyl(meth)acrylate, tetrahydrofurfuryl(meth)acrylate, an aryl(meth)acrylate hydroxyethyl(meth)acryl ate, hydroxypropyl(meth)acrylate, 2-methoxyethyl(meth)acrylate, 2-ethoxyethyl (meth) acrylate, ethylene glycol di(meth)acrylate, triethylene glycol di(meth)acrylate, 1,3-butylene glycol di(meth)acrylate, 1,6-hexanediol di(meth)acrylate, polypropylene glycol di(meth)acryl ate, trimethylol propane tri(meth)acrylate, 2-(meth)acryloyl oxyethyl phthalate, 2-(meth)acryloyl oxyethyl hexahydrophthalate, dimethylaminoethyl(meth)acrylate, dimethylaminoethyl(meth)acrylate methyl chloride, dimethylaminoethyl(meth)acrylate benzyl chloride, diethylaminoethyl(meth)acrylate, trifluoromethyl(meth)acrylate and heptadecafluorodecyl(meth)acrylate.

6. The method for handling an easily polymerizable compound according to claim 4, wherein the unsaturated aldehyde is (meth)acrolein.

7. The method for handling an easily polymerizable compound according to claim 4, wherein the flow of the second portion has a volume that is in the range from 90% to 99.5% of the total volume flow.

8. The method for handling an easily polymerizable substance according to claim 1, wherein the time between intermittent opening and closing the shutoff valve provided in the bypass line is in the range of once every eight hours to once a month.

9. The method for handling an easily polymerizable substance according to claim 1, wherein the opening and closing of the bypass shutoff valve is carried out within 10 seconds.

10. The method for handling an easily polymerizable substance according to claim 1, wherein the liquid comprising an easily polymerizable substance further comprises water and/or an organic solvent.

11. The method for handling an easily polymerizable substance according to claim 2, wherein the liquid comprising an easily polymerizable substance further comprises water and/or an organic solvent.

12. The method for handling an easily polymerizable substance according to claim 1, wherein a per cent by weight of the easily polymerizable substance in the liquid comprising an easily polymerizable substance is at least 1%.

13. The method for handling an easily polymerizable substance according to claim 2, wherein a per cent by weight of the easily polymerizable substance in the liquid comprising an easily polymerizable substance is at least 1%.

* * * * *